United States Patent [19]

Schwan et al.

[11] 4,335,130

[45] Jun. 15, 1982

[54] ANTIFUNGAL COMPOSITION

[75] Inventors: Thomas J. Schwan; Joseph E. Gray, both of Norwich, N.Y.

[73] Assignee: Morton-Norwich Products, Inc., Norwich, N.Y.

[21] Appl. No.: 263,071

[22] Filed: May 12, 1981

[51] Int. Cl.$^3$ ............................................. A01N 43/42
[52] U.S. Cl. ..................................... 424/258; 546/88
[58] Field of Search ..................... 424/258; 546/88, 81

[56] References Cited

U.S. PATENT DOCUMENTS 2,362,614 11/1944 Calva ................................... 424/325
2,617,753 11/1952 Gysin et al. ........................... 546/88
3,790,577 2/1974 Waring .................................. 546/88

OTHER PUBLICATIONS

Chemical Abstracts, vol. 93, 1980, p. 887F.
Chemical Abstracts, vol. 93, 1980, 167413u, Birss et al.
Chemical Abstracts, vol. 93, 1980, 57591t, Schaaf et al.

*Primary Examiner*—Albert T. Meyers
*Assistant Examiner*—Kin S. Chiu
*Attorney, Agent, or Firm*—Anthony J. Franze

[57] ABSTRACT

A mixture of pyrido[3,4-g]isoquinoline (A) and 3,8-phenanthroline (B) in which the ratio of A:B is 37:63 is useful as an antifungal agent.

1 Claim, No Drawings

ANTIFUNGAL COMPOSITION

This invention is concerned with a composition consisting of a mixture of two chemical compounds: pyrido[3,4-g]isoquinoline (A) and 3,8-phenanthroline (B). As produced according to the exemplary process set forth here below this mixture consists of A:B in a ratio of 37:63.

The mixture of this invention possesses antifungal properties. For example, at a concentration of 100 mcg/ml in nutritive media the growth of each of *Microsporum canis* and *Aspergillus niger* is inhibited following conventional procedure for the ascertainment of antifungal activity by in vitro techniques.

The mixture of this invention is adapted to be combined in various convenient forms such as elixirs, dusts, unguents, solutions and suspensions using conventional vehicles and adjuvants of the pharmaceutical art to provide compositions inimical to fungal growth.

In order that the composition of this invention may be readily available to and understood by those skilled in the art the following now preferred method for making it is set forth.

Cyclization of N,N'-Bis(2,2-Dimethoxyethyl)-bis-1,4-benzenemethanamine hydrochloride to a mixture of pyrido[3,4-g]isoquinoline and 3,8-phenanthroline Treatment of 130 g (0.337 mole) of the amine hydrochloride with 682 ml fuming sulfuric acid (20% $SO_3$) for 24 hr, pouring the mixture onto 7 kg of ice, adjusting the pH to 13 with 3 liters of 50% KOH, filtration to remove $K_2SO_4$, and extraction with 4×2.5 liters of chloroform gave 12 g of a brown solid. Extraction of the solid with 4×1 liter of heptane and concentration of the heptane solution to 2 liters gave 5.1 g (8.4%) of a yellow solid, m.p. 110°–117°. The nmr spectrum of the product was a composite of the spectra of pyrido[3,4-g]isoquinoline and 3,8-phenanthroline showing the ratio of the two as 37:63, respectively.

What is claimed is:

1. An antifungal mixture of pyrido[3,4-g]isoquinoline (A) and 3,8-phenanthroline (B) in which the A:B ratio is 37:63.